(12) United States Patent
Gao et al.

(10) Patent No.: US 9,276,217 B2
(45) Date of Patent: Mar. 1, 2016

(54) ELECTROACTIVE MATERIALS

(75) Inventors: Weiying Gao, Landenberg, PA (US);
Norman Herron, Newark, DE (US);
Mark A Guidry, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 377 days.

(21) Appl. No.: 13/989,253

(22) PCT Filed: Dec. 13, 2011

(86) PCT No.: PCT/US2011/064654
§ 371 (c)(1),
(2), (4) Date: May 23, 2013

(87) PCT Pub. No.: WO2012/082743
PCT Pub. Date: Jun. 21, 2012

(65) Prior Publication Data
US 2013/0240865 A1 Sep. 19, 2013

Related U.S. Application Data

(60) Provisional application No. 61/422,267, filed on Dec. 13, 2010.

(51) Int. Cl.
| | |
|---|---|
| H01L 51/00 | (2006.01) |
| H01L 51/44 | (2006.01) |
| H01L 51/50 | (2006.01) |
| C09K 11/06 | (2006.01) |
| H05B 33/10 | (2006.01) |
| C07D 209/82 | (2006.01) |

(52) U.S. Cl.
CPC .......... *H01L 51/0058* (2013.01); *C07D 209/82* (2013.01); *C09K 11/06* (2013.01); *H01L 51/006* (2013.01); *H01L 51/0061* (2013.01); *H01L 51/0072* (2013.01); *H01L 51/44* (2013.01); *H01L 51/5012* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *H01L 2251/552* (2013.01)

(58) Field of Classification Search
None
See application file for complete search history.

(56) References Cited

FOREIGN PATENT DOCUMENTS

| | | | | |
|---|---|---|---|---|
| EP | 1317005 A2 | * | 6/2003 | ............ H01L 51/20 |
| JP | 2006151844 A | * | 6/2006 | |

OTHER PUBLICATIONS

Machine English translation of JP 2006-151844 A. Jul. 29, 2015.*

*Primary Examiner* — J. L. Yang

(57) ABSTRACT

There is provided an electroactive compound having Formula I

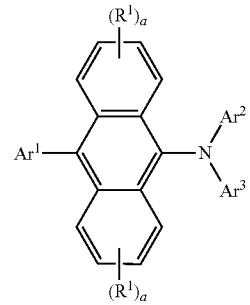

Formula I

In the formula: $Ar^1$, $Ar^2$, and $Ar^3$ are the same or different and are aryl groups; $R^1$ is the same or different at each occurrence and is D, alkyl or aryl; a is an integer from 0-4. The compound has a LUMO level deeper than −2.3 eV and a band gap of at least 2.9 eV.

13 Claims, 4 Drawing Sheets

ELECTROACTIVE MATERIALS

RELATED APPLICATION DATA

This application claims priority under 35 U.S.C. §119(e) from U.S. Provisional Application No. 61/422,267 filed on Dec. 13, 2010, which is incorporated by reference herein in its entirety.

BACKGROUND INFORMATION

1. Field of the Disclosure

This disclosure relates in general to electroactive materials and their synthesis.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. In some cases these small molecule materials are present as a dopant in a host material to improve processing and/or electronic properties.

There is a continuing need for new electroactive materials, especially for luminescent compounds that are blue-emitting.

SUMMARY

There is provided an electroactive material having Formula I

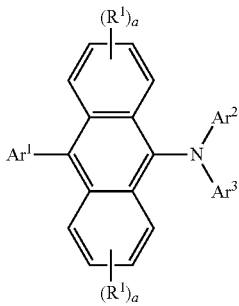

Formula I wherein:

$Ar^1$, $Ar^2$, and $Ar^3$ are the same or different and are aryl groups;

$R^1$ is the same or different at each occurrence and is D, alkyl or aryl;

a is an integer from 0-4;

and further wherein the compound has a LUMO level deeper than −2.3 eV and a band gap of at least 2.9 eV.

There is also provided an organic electronic device comprising a first electrical contact, a second electrical contact and a photoactive layer therebetween, the photoactive layer comprising the above electroactive material.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1A:
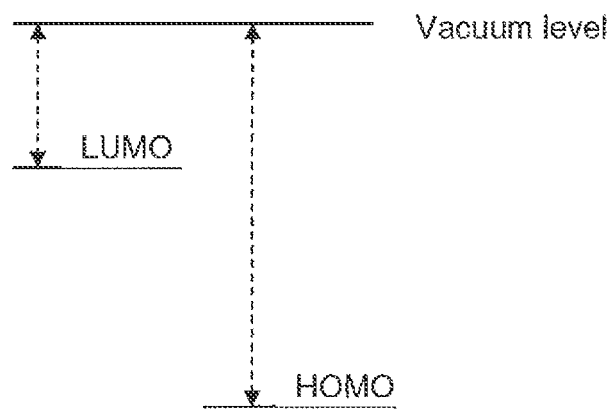
FIG. 1A includes a diagram illustrating HOMO and LUMO levels.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Materials, Synthesis, Devices, and finally Examples.

1. Definitions and Clarification of Terms

Before addressing details of embodiments described below, some terms are defined or clarified.

The term "alkoxy" is intended to mean a group having the formula —OR, which is attached via the oxygen, where R is an alkyl.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having delocalized pi electrons.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "arylene" is intended to mean a group derived from an aromatic hydrocarbon having two points of attachment. In some embodiments, an aryl group has from 3-60 carbon atoms.

The term "aryloxy" is intended to mean a group having the formula —OAr, which is attached via the oxygen, where Ar is an aryl.

The term "binaphthyl" is intended to mean a group having two naphthalene units joined by a single bond. In some embodiments, the binaphthyl group is 1,1-binaphthyl, which is attached at the 3-, 4-, or 5-position; in some embodiments, 1,2-binaphthyl, which is attached at the 3-, 4-, or 5-position on the 1-naphthyl moiety, or the 4- or 5-position on the 2-naphthyl moiety; and in some embodiments, 2,2-binaphthyl, which is attached at the 4- or 5-position.

The term "biphenyl" is intended to mean a group having two phenyl units joined by a single bond. The group can be attached at the 2-, 3-, or 4-position.

The term "carbazolyl" refers to the substituent group

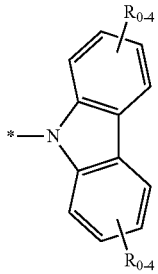

where R is D, alkyl, or aryl, and the asterisk represents the point of attachment.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The term "electron-donating" as it refers to a substituent group is intended to mean a group which adds to the electron density of an aromatic ring.

The term "electron-withdrawing" as it refers to a substituent group is intended to mean a group which decreases the electron density of an aromatic ring.

The prefix "hetero" indicates that one or more carbon atoms have been replaced with a different atom. In some embodiments, the different atom is N, O, or S.

The term "host material" is intended to mean a material, usually in the form of a layer, to which a dopant may be added.

The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 400-500 nm. In some embodiments, blue light has color coordinates of x=0.1-0.2, and y=0.01-0.3, according to the C.I.E. chromaticity scale (Commision Internationale de L'Eclairage, 1931).

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group $R_3SiO-$, where R is H, D, C1-20 alkyl, fluoroalkyl, or aryl. In some embodiments, one or more carbons in an R alkyl group are replaced with Si.

The term "silyl" refers to the group $R_3Si-$, where R is H, D, C1-20 alkyl, fluoroalkyl, or aryl. In some embodiments, one or more carbons in an R alkyl group are replaced with Si.

All groups may be unsubstituted or substituted. In some embodiments, the substituents are selected from the group consisting of halide, alkyl, alkoxy, aryl, aryloxy, silyl, siloxane, and cyano.

Figure 1B:
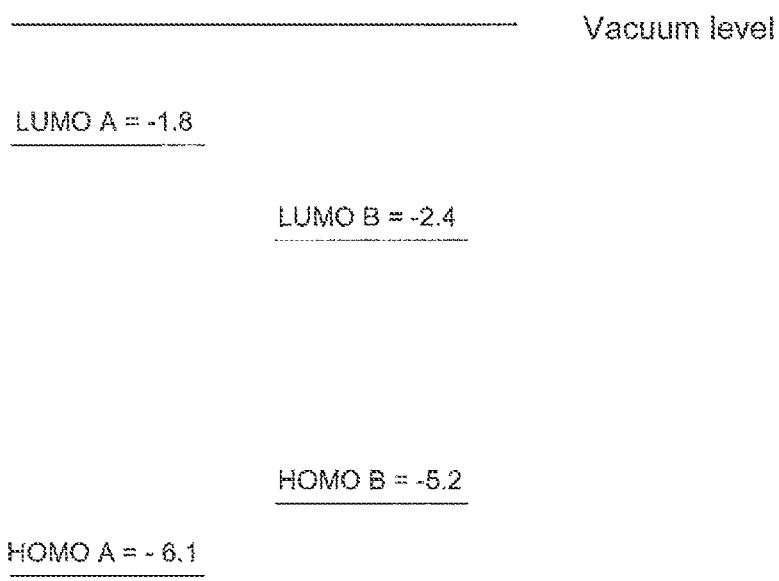
FIG. 1B includes a diagram illustrating HOMO and LUMO levels for two different materials.
Figure 1C:
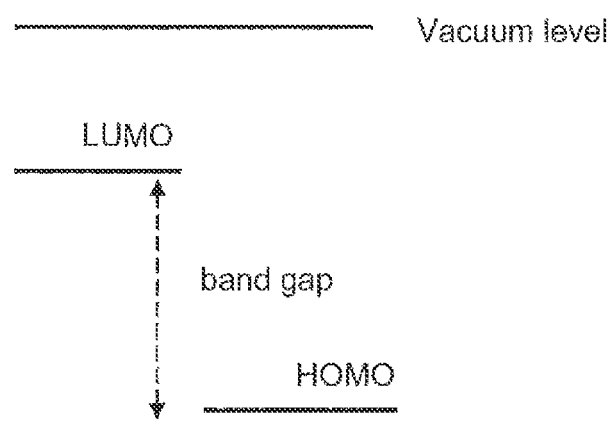
FIG. 1C includes a diagram illustrating band gap.

The energy levels are illustrated in FIGS. 1A-1C. The term "HOMO" refers to the highest occupied molecular orbital. The HOMO energy level is measured relative to vacuum level, as illustrated in FIG. 1A. By convention, the HOMO is given as a negative value, i.e. the vacuum level is set as zero and the bound electron energy levels are deeper than this. The term "LUMO" refers to the lowest unoccupied molecular orbital. The LUMO energy level is measured relative to vacuum level in eV, as illustrated in FIG. 1A. By convention, the LUMO is a negative value, i.e. the vacuum level is set as zero and the bound electron energy levels are deeper than this. By "shallower" it is meant that an energy level is closer to the vacuum level. This is illustrated in FIG. 1B, where HOMO B is shallower than HOMO A. By "deeper" it is meant than an energy level is farther removed from vacuum level. This is illustrated in FIG. 1B, where LUMO B is deeper than LUMO A. The term "band gap" refers to the difference in energy between the HOMO and LUMO levels of a material, as shown in FIG. 1C. The band gap is reported as a positive number in eV.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81*st* Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Materials

The new electroactive materials described herein have Formula I

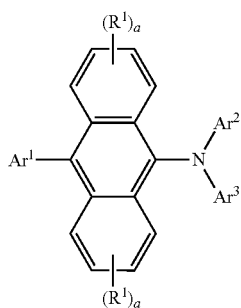

Formula I wherein:
  $Ar^1$, $Ar^2$, and $Ar^3$ are the same or different and are aryl groups;
  $R^1$ is the same or different at each occurrence and is D, alkyl or aryl;
  a is an integer from 0-4;
and further wherein the compound has a LUMO level deeper than −2.3 eV and a band gap of at least 2.9 eV.

In some embodiments, the compounds having Formula I or Formula II are useful as electron-trapping materials. Electron trapper materials have been added to standard blue emissive systems to try to decrease electron flow in the blue sub-pixel stack. These materials have deep lying LUMO positions which confine negative charge and retard electron flow through the stack. This brings the charge balance back into alignment and improves lifetime of the device significantly. However, previous such materials (eg C60) have all suffered from a strong quenching of the blue excitons leading to drops in quantum efficiency which are unacceptable. A material having a deep LUMO (strong electron trap) coupled with a wide gap (exciton energy such that the material is not a quencher for the blue photons) is desired.

In some embodiments, the compounds having Formula I or Formula II have a LUMO level deeper than −2.4 eV; in some embodiments, deeper than −2.5 eV. In some embodiments, the compounds having Formula I or Formula II have a band gap of at least 3.0 eV; in some embodiments, at least 3.1 eV.

In some embodiments, the compounds having Formula I or Formula II are useful as emissive materials. In some embodiments, the compounds are blue emissive materials. They can be used alone or as a dopant in a host material.

In some embodiments, the compound having Formula I is deuterated. In some embodiments, the compound is at least 10% deuterated. By "% deuterated" or "% deuteration" is meant the ratio of deuterons to the total of hydrogens plus deuterons, expressed as a percentage. The deuteriums may be on the same or different groups. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, $Ar^1$ is phenyl, biphenyl, naphthyl, binaphthyl, phenylnaphthyl, naphthylphenyl, substituted derivatives thereof, or deuterated analogs thereof. In some embodiments, the substituted derivative has a substituent selected from the group consisting of D, alkyl, aryl, deuterated analogs thereof, and combinations thereof. $Ar^1$ is not substituted with an amino group.

In some embodiments, $Ar^2$ and $Ar^3$ are phenyl, biphenyl, naphthyl, binaphthyl, phenylnaphthyl, naphthylphenyl, carbazolylphenyl, diarylaminophenyl, substituted derivatives thereof, or deuterated analogs thereof, where there is at least one substituent which is an electron-withdrawing group ("EWG"). In some embodiments, the EWG is fluoro, cyano, nitro, where R is alkyl or perfluoroalkyl, or deuterated analogs thereof.

In some embodiments, the compound of Formula I can be further described by Formula II

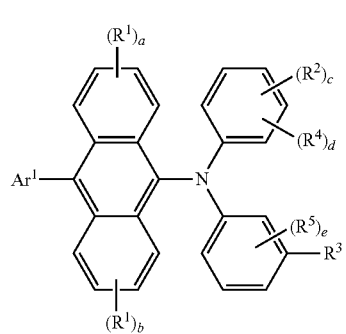

Formula II wherein:
Ar$^1$ is an aryl group;
R$^1$ is the same or different at each occurrence and is D, alkyl or aryl;
R$^2$ is an electron-withdrawing group;
R$^3$ is H, D, carbazolyl, diarylamino, an electron-withdrawing group, or a deuterated analog thereof
R$^4$ is the same or different at each occurrence and is D, alkyl, alkoxy, silyl, siloxane, an electron withdrawing group, or a deuterated analog thereof;
R$^5$ is the same or different at each occurrence and is D, alkyl, alkoxy, silyl, siloxane, an electron-withdrawing group, or a deuterated analog thereof;
a is an integer from 0 to 4;
b is an integer from 0 to 4;
c is an integer from 1 to 5;
d is an integer from 0 to 4, such that c+d≤5; and
e is an integer from 0 to 4.

The compound of Formula II has a LUMO level deeper than −2.3 eV and a band gap of at least 2.9 eV.

In some embodiments of Formula II, Ar$^1$ is phenyl, biphenyl, naphthyl, binaphthyl, phenylnaphthyl, naphthylphenyl, a substituted derivative thereof, or a deuterated analog thereof. In some embodiments, the substituted derivative has a substituent selected from the group consisting of D, alkyl, aryl, deuterated analogs thereof, and combinations thereof. Ar$^1$ is not substituted with an amino group.

In some embodiments of Formula II, R$^1$=D and a and b are both greater than 0. In some embodiments, R$^1$=D and a=b=4. In some embodiments, a=b=0.

In some embodiments of Formula II, R$^2$ is cyano, nitro, or —SO$_2$R, where R is alkyl.

In some embodiments of Formula II, R$^3$ is carbazolyl, diphenylamino, or a deuterated analog thereof.

In some embodiments of Formula II, d>0 and R$^4$ is an EWG. In some embodiments, R$^4$ is cyano, nitro, or —SO$_2$R, where R is alkyl. In some embodiments, d=0.

In some embodiments of Formula II, e=0.

In some embodiments of Formula II, d=1 and R$^2$=R$^4$=CN.

In some embodiments of Formula II, there can be any combination of the following: (i) Ar$^1$ is phenyl, biphenyl, naphthyl, binaphthyl, phenylnaphthyl, naphthylphenyl, a substituted derivative thereof, or a deuterated analog thereof, wherein Ar$^1$ does not have an amino substituent; (ii) R$^1$=D and a and b are both greater than 0; (iii) R$^2$ is cyano, nitro, or —SO$_2$R, where R is alkyl; (iv) R$^3$ is carbazolyl, diphenylamino, or a deuterated analog thereof; (v) d>0 and R$^4$ is an EWG; and (vi) e=0. In some embodiments, R$^4$ is cyano, nitro, or where R is alkyl.

In some embodiments of Formula II, d=0 and further there can be any combination of the following: (i) Ar$^1$ is phenyl, biphenyl, naphthyl, binaphthyl, phenylnaphthyl, naphthylphenyl, a substituted derivative thereof, or a deuterated analog thereof, wherein Ar$^1$ does not have an amino substituent; (ii) R$^1$=0 and a and b are both greater than 0; (iii) R$^2$ is cyano, nitro, or —SO$_2$R, where R is alkyl; (iv) R$^3$ is carbazolyl, diphenylamino, or a deuterated analog thereof; (v) d>0 and R$^4$ is an EWG; and (vi) e=0.

Examples of electroactive materials having Formula I or Formula II include, but are not limited to, compounds B1 through B11 shown below. The LUMO and band gap values listed were calculated. All calculations were performed with the density functional theory (DFT) methods within the Gaussian 03 suite of programs. (Gaussian 03, revision D.01; Gaussian, Inc., Wallingford, Conn., 2004). The molecular structures were first optimized at the BP86/6-31G+IrMWB60 level and then used in subsequent analytic vibrational frequency calculations at this same level of computation to ensure that these structures were indeed equilibrium ones. For the excited-state calculations, previous experience has shown that time-dependent DFT (TDDFT) at the B3LYP/6-31G+IrMWB60 level is satisfactory in computing the first seven singlet and triplet energy transitions. In order to obtain HOMO and LUMO values for these molecules, the B3LYP/6-31+G(d)+IrMWB60 level was used.

Compound B1

LUMO = −2.45 eV; band gap = 3.13 eV

Compound B2

LUMO = −2.52 eV; band gap = 3.12 eV

Compound B3

LUMO = −2.64 eV; band gap = 3.11 eV

-continued
Compound B4
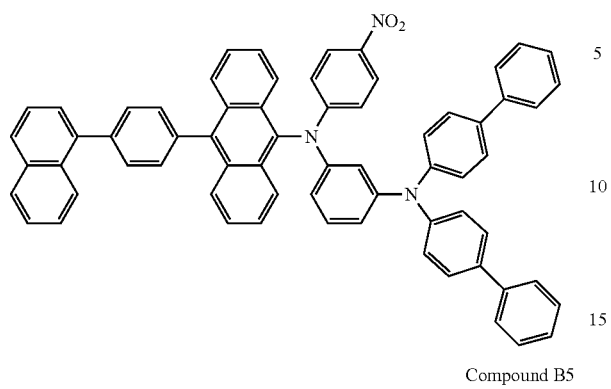
Compound B5
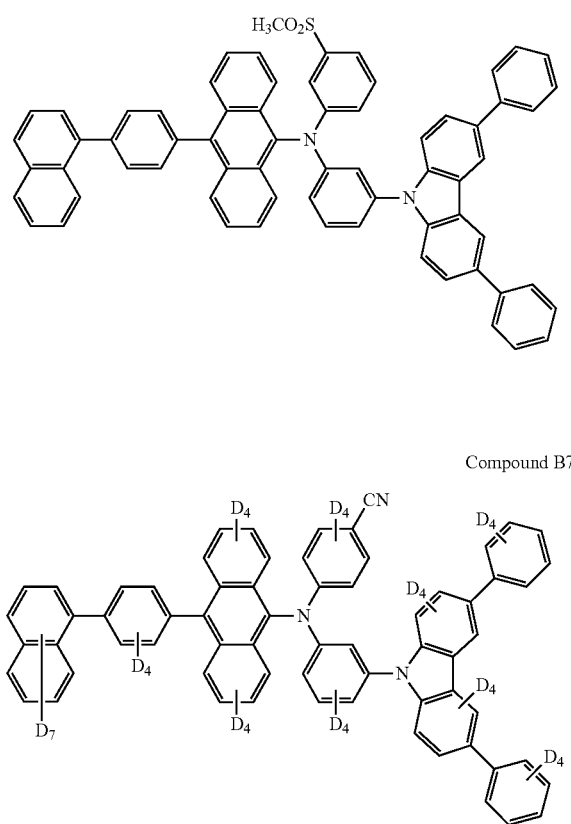
Compound B6
Compound B7
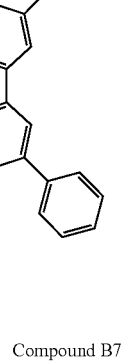
-continued
Compound B8
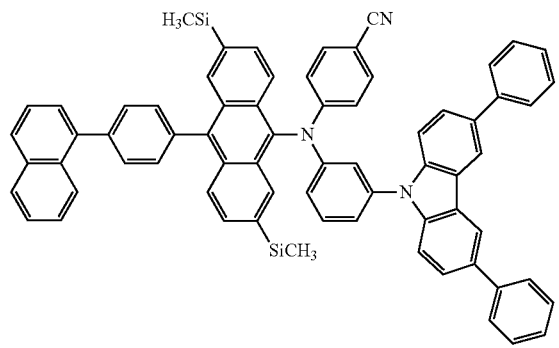
Compound B9
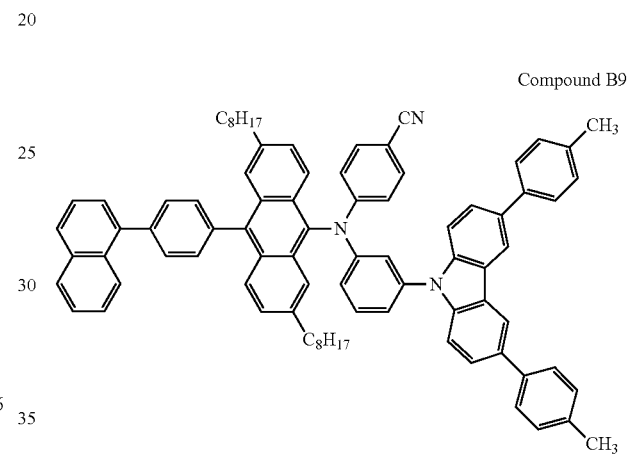
Compound B10
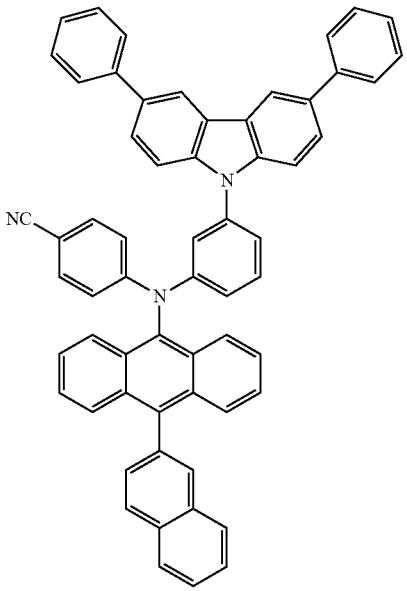
LUMO = -2.54 eV; band gap = 2.99 eV -continued

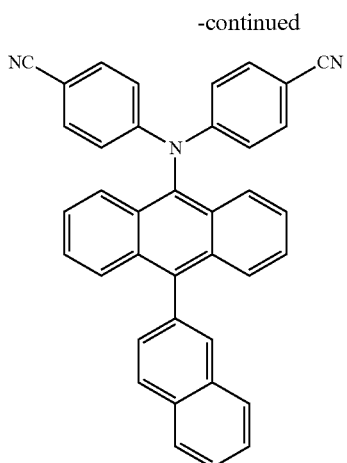

Compound B11

LUMO = −2.68 eV; band gap = 3.18 eV

3. Synthesis

The electroactive materials described herein, are generally prepared according to the following scheme:

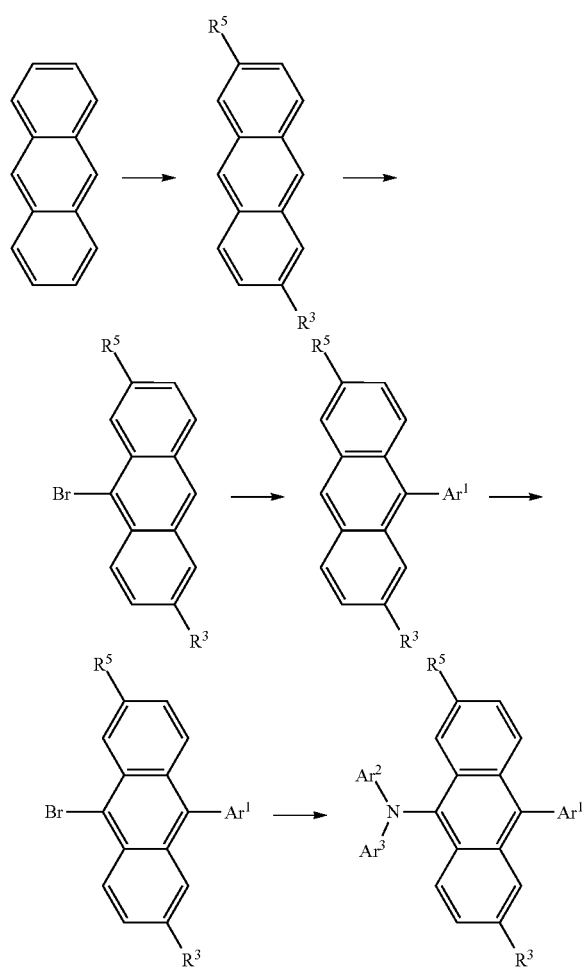

When $R^3=R^5$, the first step involves alkylation of anthracene using Friedel Crafts chemistry with the appropriate alcohol, for example, t-butanol, 1-adamantanol or 1-methylcyclohexanol. This can be carried out in a solvent such as neat trifluoroacetic acid, generally with heating, followed by isolation and chromatographic purification. For some of the compounds, the substituted anthracene is commercially available, such as 2-t-butylanthracene.

The substituted anthracene can then be monobrominated, such as by using N-bromosuccinamide in $CCl_4$.

The brominated product is then reacted with the appropriate aryl boronic acid in a Suzuki type reaction using a Pd catalyst.

The product is then brominated again using $Br_2$ in $CCl_4$

The brominated product is then reacted with the appropriate amine with a Pd catalyst. The amine itself can also be prepared by Pd catalyzed amination.

In cases where the $R^3=R^5$=alkoxy group, the substituted anthracene intermediate can be prepared by etherification of 2,6-dihydroxyanthraquinone, followed by hydride reduction.

4. Devices

Organic electronic devices that may benefit from having one or more layers comprising the electroactive materials described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semiconductor layers (e.g., a transistor or diode).

Figure 2:
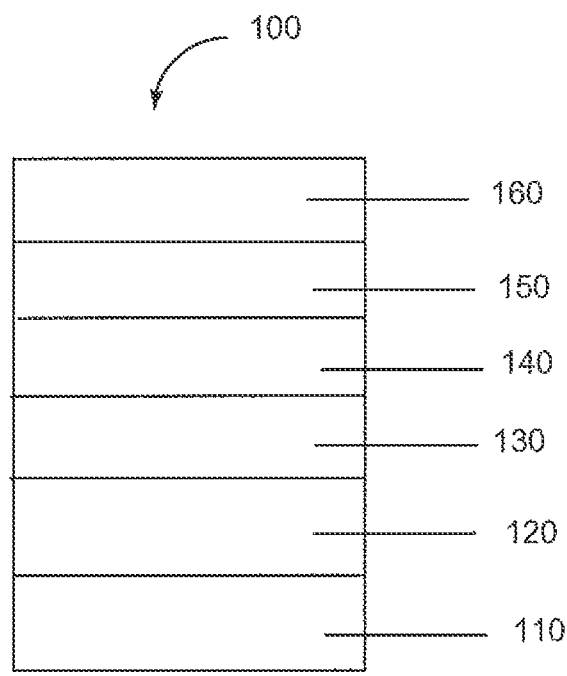
FIG. 2 includes an illustration of an organic light-emitting device.

One illustration of an organic electronic device structure is shown in FIG. 2. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

Figure 3:
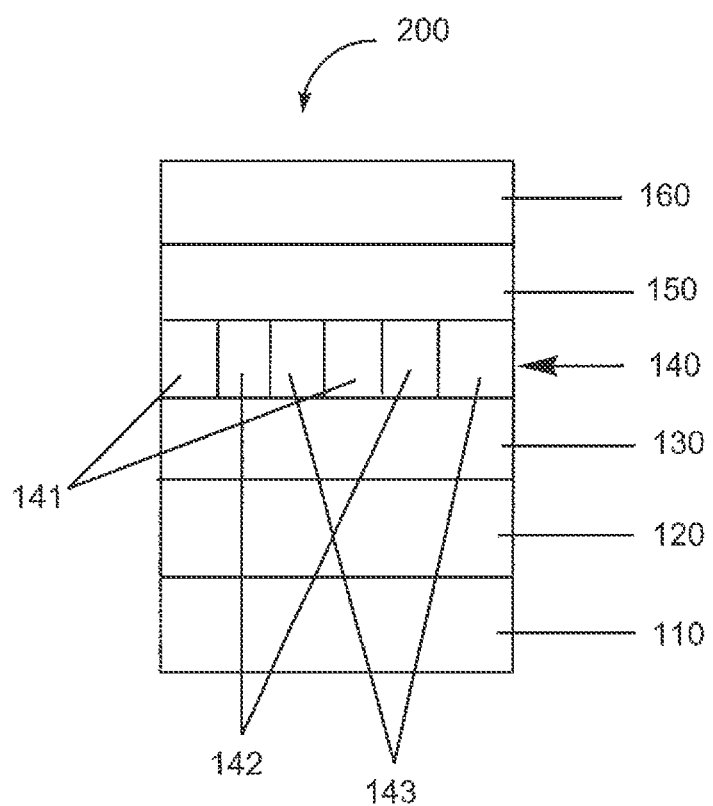
FIG. 3 includes another illustration of an organic light-emitting device.

In some embodiments, the photoactive layer is pixellated, as shown in FIG. 3. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I or Formula II are useful as the emissive material in photoactive layer 140, having blue emission color. They can be used alone or as a dopant in a host material.

In some embodiments, the compounds having Formula I or Formula II are useful as electron-trapping materials in photoactive layer 140.

a. Photoactive Layer

In some embodiments, the photoactive layer comprises a host material and an electroactive compound having Formula I or Formula II as a dopant. In some embodiments, a second host material may be present.

In some embodiments, the photoactive layer consists essentially of a host material and an electroactive compound having Formula I or Formula II as a dopant. In some embodiments, the photoactive layer consists essentially of a first host material, a second host material, and an electroactive compound having Formula I or Formula II as a dopant. The weight ratio of dopant to total host material is in the range of 5:95 to 70:30; in some embodiments, 90:10 to 80:20.

In some embodiments, the photoactive layer comprises a blue luminescent compound, a host material, and an electroactive compound having Formula I or Formula II as an electron-trap material. In some embodiments, the photoactive layer consists essentially of a blue luminescent compound, a host material, and a compound having Formula I or Formula II as an electron-trap material. The electron-trap material of Formula I or Formula II can be present in an amount of 1-10 wt % based on the total weight of the layer; in some embodiments, 2-5 wt %.

In some embodiments, the host is a bis-condensed cyclic aromatic compound.

In some embodiments, the host is an anthracene derivative compound. In some embodiments the compound has the formula:

An-L-An where:
An is an anthracene moiety;
L is a divalent connecting group.

In some embodiments of this formula, L is a single bond, —O—, —S—, —N(R)—, or an aromatic group. In some embodiments, An is a mono- or diphenylanthryl moiety.

In some embodiments, the host has the formula:

A-An-A where:
An is an anthracene moiety;
A is an aromatic group.

In some embodiments, the host is a diarylanthracene. In some embodiments the compound is symmetrical and in some embodiments the compound is non-symmetrical.

In some embodiments, the host has the formula:

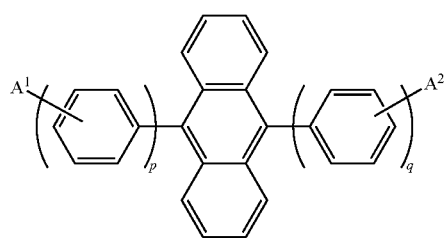

where:
$A^1$ and $A^2$ are the same or different at each occurrence and are selected from the group consisting of H, an aromatic group, and an alkenyl group, or A may represent one or more fused aromatic rings;
p and q are the same or different and are an integer from 1-3.

In some embodiments, the anthracene derivative is non-symmetrical. In some embodiments, p=2 and q=1. In some embodiments, at least one of $A^1$ and $A^2$ is a naphthyl group.

In some embodiments, the host is selected from the group consisting of

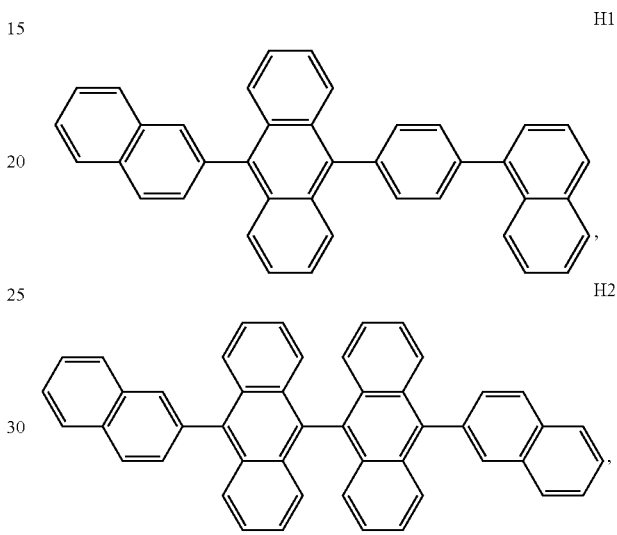

deuterated derivatives thereof, and combinations thereof.

Examples of other blue light-emitting materials include, but are not limited to, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N'N'-2,5-phenylenediamine (FDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-O-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. The hole injection material can be present in the liquid medium in an amount from 0.5 to 10 percent by weight. The hole injection layer can be applied by any continuous or discontinuous liquid deposition technique. In one embodiment, the hole injection layer is applied by spin coating. In one embodiment, the hole injection layer is applied by ink jet printing. In one embodiment, the hole injection layer is applied by continuous nozzle printing. In one embodiment, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In one embodiment, the hole transport layer is applied by spin coating. In one embodiment, the hole transport layer is applied by ink jet printing. In one embodiment, the hole transport layer is applied by continuous nozzle printing. In one embodiment, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. In one embodiment, the photoactive layer is applied by continuous nozzle printing. In one embodiment, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In one embodiment, it is deposited by thermal evaporation under vacuum.

The electron injection layer can be deposited by any vapor deposition method. In one embodiment, it is deposited by thermal evaporation under vacuum.

The cathode can be deposited by any vapor deposition method. In one embodiment, it is deposited by thermal evaporation under vacuum.

EXAMPLES

The concepts described herein will be further described in the following examples, which do not limit the scope of the invention described in the claims.

Example 1

This example illustrates the preparation of Compound B1.

(1a) Preparation of 9-bromo-10-(4-(1-naphthyl)phenyl)-anthracene

This intermediate can be made according to the following scheme:

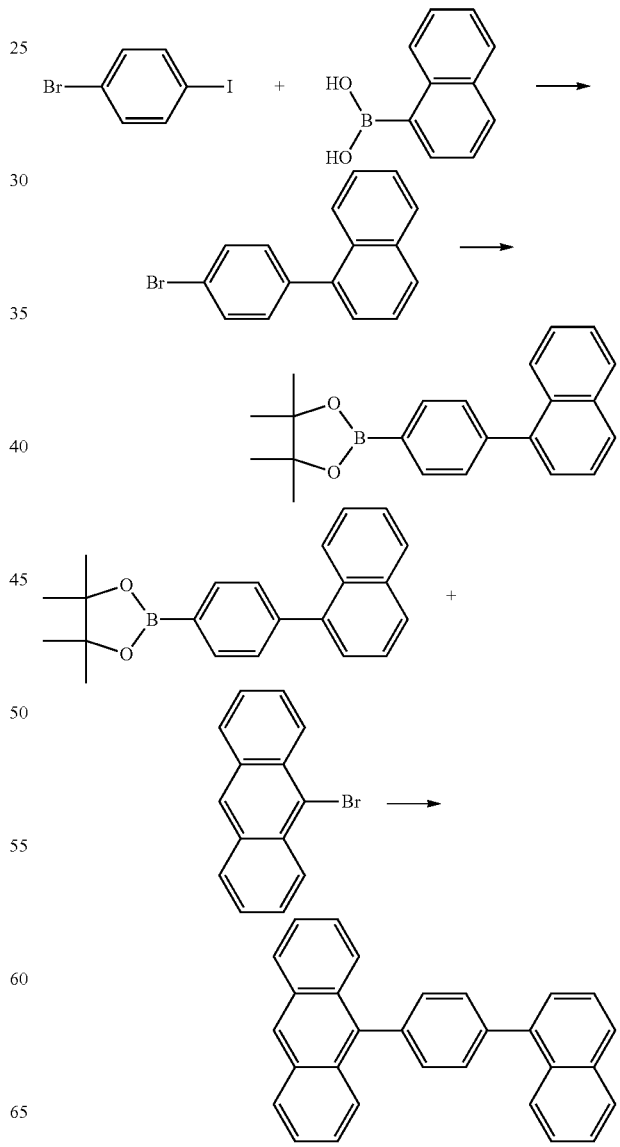

-continued

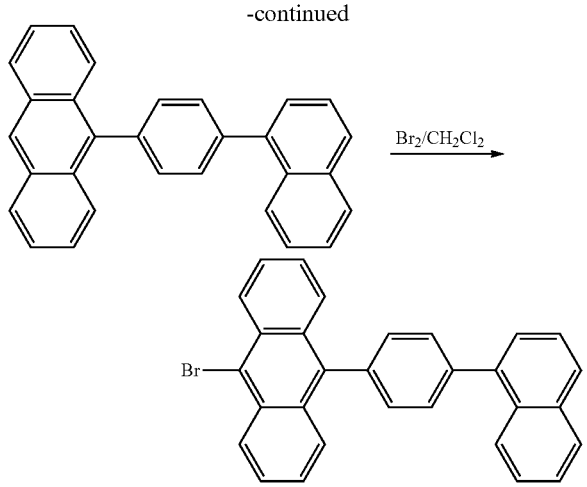

To a 500 mL round bottom flask equipped with a stir bar in a nitrogen-filled glove box were added naphthalen-1-yl-1-boronic (14.2 g, 82.6 mmol), acid, 1-bromo-2-iodobenzene (25.8 g, 91.2 mmol), tetrakis(triphenylphospine) palladium (0) (1.2 g, 1.4 mmol), sodium carbonate (25.4 g, 240 mmol), and toluene (120 mL). After removal from the dry box, the reaction mixture was purged with nitrogen and degassed water (120 mL) was added by syringe. The reaction flask was then fitted with a condenser and the reaction was refluxed for 15 hours. The reaction was monitored by TLC. The reaction mixture was cooled to room temperature. The organic layer was separated and the aqueous layer was extracted with DCM. The organic fractions were combined and the solvent was removed under reduced pressure to give a yellow oil. Purification by column chromatography using silica gel afforded 13.6 g of a clear oil (58%).

To a 1-liter flask equipped with a magnetic stirring bar, a reflux condenser that was connected to a nitrogen line and an oil bath, were added 4-bromophenyl-1-naphthalene (28.4 g, 10.0 mmol), bis(pinacolate) diboron (40.8 g, 16.0 mmol), Pd(dppf)$_2$Cl$_2$ (1.64 g, 2.0 mmol), potassium acetate (19.7 g, 200 mmol), and DMSO (350 mL). The mixture was bubbled with nitrogen for 15 min and then Pd(dppf)$_2$Cl$_2$ (1.64 g, 0.002 mol) was added. During the process the mixture turned to a dark brown color gradually. The reaction was stirred at 120° C. (oil bath) under nitrogen for 18 h. After cooling the mixture was poured into ice water and extracted with chloroform (3×). The organic layer was washed with water (3×) and saturated brine (1×) and dried with MgSO4. After filtration and removal of solvent, the residue was purified by chromatography on a silica gel column. The product containing fractions were combined and the solvent was removed by rotary evaporation. The resulting white solid was crystallized from hexane/chloroform and dried in a vacuum oven at 40° C. to give the product as white crystalline flakes (15.0 g in 45% yield). 1H and 13C-NMR spectra are in consistent with the expected structure.

The boronic ester is added to 9-bromoanthracene in toluene. To this is added Na$_2$CO$_3$, H$_2$O (120 mL), and a quaternary ammonium compound. The mixture is bubbled with nitrogen and Pd(PPh$_3$)4 is added. The mixture is refluxed for 12 h under a nitrogen atmosphere. After cooling down the reaction mixture was separated, the organic layer is washed with water and separated, dried and concentrated to and poured into MeOH. The solid is filtered to give a yellow crude product which is redissolved in CHCl$_3$, dried over MgSO4, filtered. The filtrate is purified on silica gel using hexane only as eluent to give the white product.

Into a ice-bath cooled solution of 9-(4-naphthalen-1-yl) phenylanthracene in CH$_2$Cl$_2$ is added slowly bromine dissolved in CH2Cl2. The reaction immediately occurs and the color changes to light yellow. A solution of Na2S2O3 is added and stirred for 15 min. The organic phase is separated, washed by Na2CO3, and water. The organic phase is separated, dried, evaporated, poured into methanol and filtered to give 9-bromo-10-(4-(1-naphthyl)phenyl)-anthracene.

(1b) Preparation of 3-(9-carbazolyl)-phenyl bromide

Mix together 0.4 g Pd2DBA3 (DBA dibenzylideneacetone) and 0.4 g DPPF (DPPF 1,1'-bis(diphenylphosphino) ferrocene) and 4.3 g sodium t-butoxide and dissolve into 200 mL xylenes in glove box. Stir 15 mins then add 25 g of 3-iodo-bromobenzene. Stir 15 mins then add 5 g carbazole and the mix was brought to reflux. Reflux overnight using an air condensor in glove box. The solution immediately is dark purple/brown but on reaching ~80 C. it is dark reddish brown and cloudy. After heating close to reflux overnight, the solution is dark brown and clear. Evaporated outside the glove box in rotovap and then dissolved in DCM and extracted (soxhlet) through a bed of silica and basic alumina (stacked in soxhlet) using DCM. Collect dark orange solution and evaporate to dryness. Leaves a dark orange oil. Wash with methanol and then dissolve into ether and reprecipitated with methanol—this product is slightly soluble in methanol.

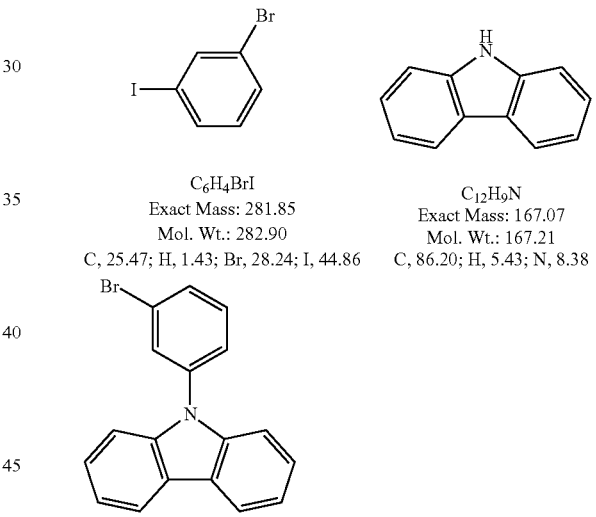

Take orange brown oil and evaporate to low volume in ether and then add a little acetone/methanol to ppt an off-white solid in yield of ~3.2 g. Collect by filtration and wash with a little acetone and suction dry. The structure was confirmed by 1-H nmr spectroscopy.

(1c) Preparation of 3-(9-carbazolyl)-aniline 8.5 g 9-(3-bromophenyl)-carbazole from step (1b) above, 0.12 g Pd2DBA3 0.11 g dicyclohexylphosphinebiphenyl and 50 mL dioxane were stirred in a glove box (N2). 9.2 g LiN[Si(Me)3]2 and a further 10 mL dioxane were added and the reaction brought to reflux overnight. The reaction was cooled and remove from the glove and water was added slowly. The pH of the aqueous layer was brought to 9 with carbonate and then the mixture was extracted with DCM. The DCM layer was separated and dried over magnesium sulfate then chromatographed on silica eluting with 1:1 ethylacetate:hexanes. The product elutes as a tan solution which on evaporation and addition of methanol produces a tan colored crystalline solid in ~90% yield. 1-H nmr shows it to be the desired aniline product.

(1d) Preparation of 3-(9-carbazolyl)-phenyl,9-anthracenyl amine

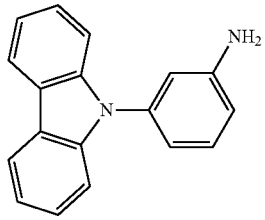

$C_{16}H_{14}N_2$
Exact Mass: 258.12
Mol. Wt.: 258.32
C, 83.69; H, 5.46; N, 10.84

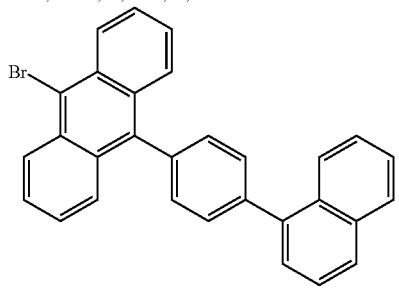

$C_{30}H_{19}Br$
Exact Mass: 458.07
Mol. Wt.: 459.38
C, 78.44; H, 4.17; Br, 17.39

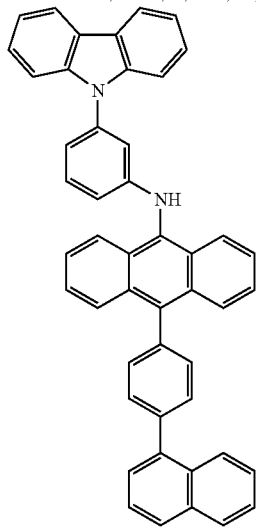

$C_{48}H_{32}N_2$
Exact Mass: 636.28
Mol. Wt.: 636.78
C, 90.54; H, 5.07; N, 4.40

Take 1.3 g of the carbazole from step (1c) above (0.005M) in glove box and add 2.3 g anthracene from step (a) above (0.005M). Add 0.05 g Pd2DBA3 (0.05 mM), 0.022 g P(t-Bu)₃ (0.11 mM) and 0.55 g t-BuONa and dissolve all into 25 mL toluene. Upon addition of catalyst materials, there is a mild exotherm. Heat in glove box in mantle at 80 C. under nitrogen for 2 hr as a dark brown solution (thick). Cool and work up by basic-alumina chromatography eluting with DCM and collect dark yellow solution with bright purple/blue PL. Evap to a very dark oily solid. Wash with methanol to give a nice powdery yellow solid. Rinse recovered solid with methanol to give ~1.8 g of yellow solid. The structure was confirmed by 1-H nmr spectroscopy.

(1e) Preparation of Compound B1

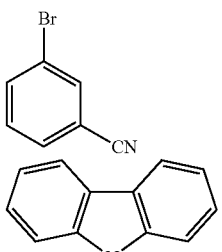
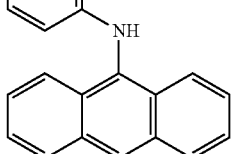
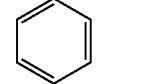
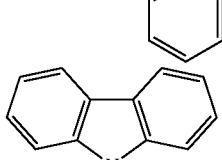
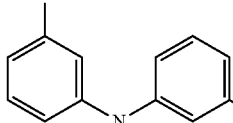
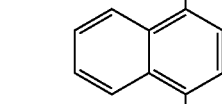
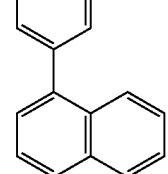

Take 0.64 g of the carbazoleanthracene (0.001M) (from step (1d) above) in glove box and add 0.36 g bromophenylnitrile (0.002M). Add 0.1 g Pd2DBA3 (0.1 mM), 0.045 g P(t-Bu)3 (0.22 mM) and 0.25 g t-BuONa and dissolve all into 25 mL toluene. Upon addition of catalyst materials, there is a mild exotherm. Heat in glove box in mantle at 800 under nitrogen for 2 hr as a dark brown solution then maintain at 800 overnight under nitrogen. Cool and work up by B-alumina chromatography eluting with DCM/methanol (materials sticks badly without methanol co-eluent) and collect yellow solution with bright purple/blue PL. Evap to a very dark oily solid. Wash with methanol to give a powdery tan yellow solid. Rinse recovered solid with methanol to give ~0.3 g of yellow solid which was then chromatographed on silica eluting with chloroform to give a bright yellow band with blue PL. Collect and evap then add methanol to deliver 0.25 g pale yellow solid. The structure was confirmed by 1-H nmr spectroscopy.

Example 2

This example illustrates the preparation of Compound B2.

(2a) Preparation of 3,6-diphenylcarbazole 25 g 3,6-dibromocarbazole and 20.5 g phenylboronic acid were mixed in 150 mL water and 300 mL dioxane in glove box. Stir vigorously and add 45 g sodium carbonate. Finally add 3 g Pd2DBA3 and 1.5 g tri-t-butylphosphine. Stir and reflux overnight then cool and remove from glove box. Add water to precipitate white solid then filter and collect. Dissolve in dichloromethane and chromatograph on silica eluting with DCM:hexanes 1:2 and elute product as colorless solution which on evaporation and washing with hexanes gives the desired product in ~80% yield as a fluffy white solid.

(2b) Preparation of
3-(3,6-diphenyl-9-carbazolyl)-bromobenzene

Mix together 0.4 g Pd2DBA3 and 0.4 g DPPF and 4.3 g sodium t-butoxide and dissolve into 200 mL xylenes in glove box. Stir 15 mins then add 25 g of 3-iodo-bromobenzene. Stir 15 mins then add 10 g carbazole and the mix brought to reflux. Reflux o/n. using an air condensor. Solution immediately is dark purple/brown but on reaching ~80 C. it is dark reddish brown and cloudy. After heating close to reflux overnight, the solution is dark brown and clear. Evaporated outside the glove box in rotovap and then dissolved in DCM and extracted (soxhlet) through a bed of silica and basic alumina (stacked in soxhlet) using DCM. Collect dark orange solution and evaporate to dryness. Leaves a dark orange oil. Wash with methanol and then dissolve into ether and reprecipitate with methanol.

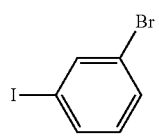

$C_6H_4BrI$
Exact Mass: 281.85
Mol. Wt.: 282.90
C, 25.47; H, 1.43: Br, 28.24; I, 44.86

-continued

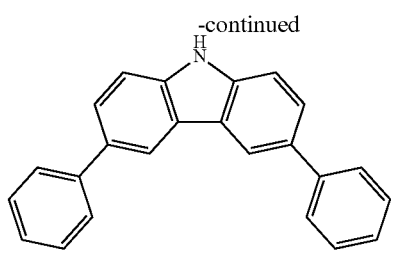

$C_{24}H_{17}N$
Exact Mass: 319.14
Mol. Wt.: 319.40
C, 90.25; H, 5.36; N, 4.39

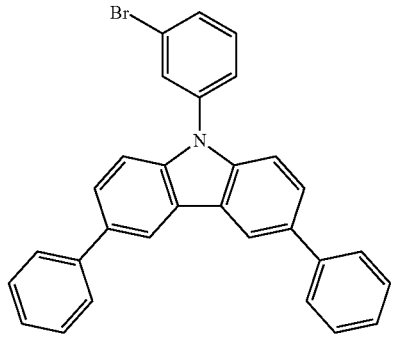

$C_{30}H_{20}BrN$
Exact Mass: 473.08
Mol. Wt.: 474.39
C, 75.95; H, 4.25; Br, 16.84; N, 2.95

Take orange brown oil and evaporate to low volume in ether and then add a little acetone/methanol to precipitate an off-white solid in yield of ~6.4 g. Collect by filtration and wash with a little acetone and suction dry. The structure was confirmed by 1-H nmr spectroscopy.

(2c) Preparation of 4-cyanophenyl,3-(3,6-diphenyl-9-carbazolyl)phenylaniline 9.0 g of carbazole from step (2b) above and 2.23 g 4-aminobenzonitrile were mixed in 60 mL toluene in nitrogen filled glove box. 0.4 g Pd2DBA3 and 0.18 g tri-t-butylphosphine were added followed quickly by 1.81 g t-BuONa. The mixture was heated briefly to reflux then held at 80° C. overnight in the glove box with vigorous stirring. After cooling the reaction was chromatographed on silica using a gradient of DCM:hexanes (1:4 to 4:1) to elute the product which upon concentration and addition of hexanes precipitated the desired product in ~80% yield (~6.5 g) with structure confirmed by 1-H nmr spectroscopy.

(2d) Preparation of Compound B2

Take 0.45 g of the monobromoanthracene (from step (1a) of Example 1 above) (0.5 mM) in glove box and add 0.52 g (0.5 mM) sec amine (from Pt 2.3) and 0.1 g t-BuONa (1 mM) with 10 mL toluene. Add 0.1 g Pd2DBA3 (0.1 mM), 0.05 g P(t-Bu)3 (0.2 mM) dissolved in toluene. Mix and heat in glove box in mantle at 80 C. under nitrogen for 1 hr. Solution immediately is dark purple but on reaching ~80 C. it is dark red brown. Warm at 80 C. overnight with stirring in glove box. Cool and work up by removing from glove box and filter through an acidic alumina plug eluting with toluene. Product is pale yellow/orange and quite soluble as a greenish blue PL band Rechromatograph on silica/florisil with toluene eluent. Elutes an orange band first with little PL followed by a yellow band with bright blue PL. This second fraction was evaporated to low volume and methanol added to ppt a yellow solid with blue PL in ~0.45 g yield. The material was collected by filtration and washed with heptane and suction dried. Material is soluble in toluene. The structure was confirmed by 1-H nmr spectroscopy.

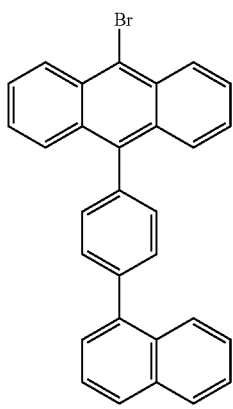

C₃₀H₁₉Br
Exact Mass: 458.07
Mol. Wt.: 459.38
C, 78.44; H, 4.17; Br, 17.39

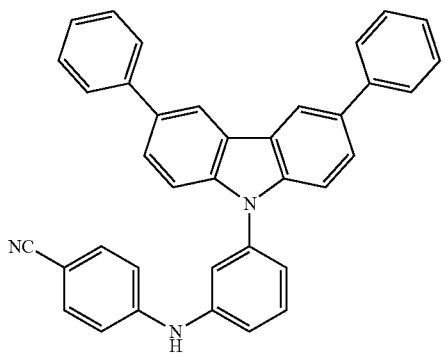

C₃₇H₂₅N₃
Exact Mass: 511.20
Mol. Wt.: 511.61
C, 86.86; H, 4.93; N, 8.21

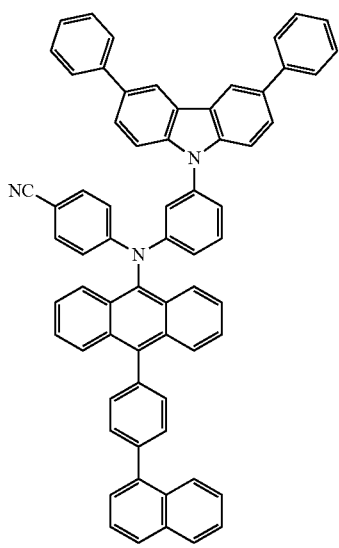

C₅₇H₄₆N₃
Exact Mass: 889.35
Mol. Wt.: 890.08
C, 90.41; H, 4.87; N, 4.72

Example 3

This example illustrates the preparation of Compound B3.

(3a) Preparation of 3,5-dicyanophenyl,3-(3,6-diphenyl-9-carbazolyl)phenylaniline 9.0 g of carbazole from step (2b) from Example 2 above and 2.7 g 5-aminoisophthalonitrile were mixed in 50 mL toluene in nitrogen filled glove box. 0.2 g Pd2DBA3 and 0.09 g tri-t-butylphosphinewere added followed quickly by 1.81 g t-BuONa. The mixture was heated briefly to reflux then held at 80° C. overnight in the glove box with vigorous stirring. After cooling the reaction was chromatographed on silica using a gradient of DCM:hexanes (1:4 to 4:1) to elute the product which upon concentration and addition of hexanes precipitated the desired product in 50% yield (~4 g) with structure confirmed by 1-H nmr spectroscopy.

(3b) Preparation of Compound B3

Take 1.5 g g of the monobromoanthracene (from step (1a) from Example 1 above) (1.5 mM) in glove box and add 2.03 g (~1.8 mM) sec amine (from step (3a) above) and 0.3 g t-BuONa (3 mM) with 10 mL toluene. Add 0.3 g Pd2DBA3 (0.3 mM), 0.15 g P(t-Bu)3 (0.6 mM) dissolved in toluene. Mix and heat in glove box in mantle at 80 C. under nitrogen for 1 hr. Solution immediately is dark purple but on reaching ~80 C. it is dark red brown. Hold at 80 C. under nitrogen with vigorous stirring overnight. Cool and work up by removing from glove box and filter through a basic alumina plug eluting with toluene. Product is pale yellow/orange and quite soluble as a greenish blue PL band Rechromatograph on silica/florisil with toluene eluent. Elutes an orange band first with little PL followed by a yellow band with bright blue PL which was evaporated to low volume and add methanol to ppt yellow solid with blue PL in ~0.45 g yield. Filter, collect and wash with heptanes before suction drying. Material is soluble in toluene. The structure was confirmed by 1-H nmr spectroscopy. The material was further purified on 1300 flash chromatography system and recrystallized to yield 250 mg. Recrystallized again from toluene/ethanol and then toluene/heptanes as a pale lemon yellow powder with bright blue PL in toluene solution.

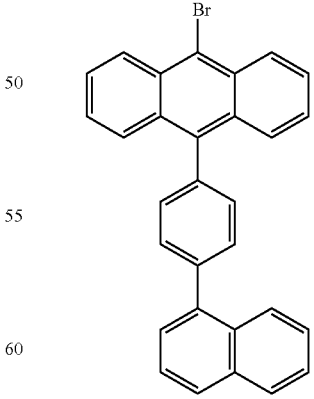

C₃₀H₁₉Br
Exact Mass: 458.07
Mol. Wt.: 459.38
C, 78.44; H, 4.17; Br, 17.39

-continued

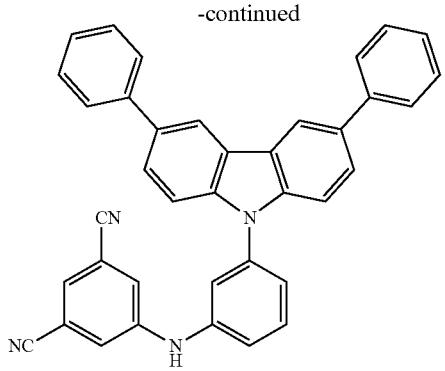

C_38H_24N_4
Exact Mass: 536.20
Mol. Wt.: 536.62
C, 85.05; H, 4.51; N, 10.44

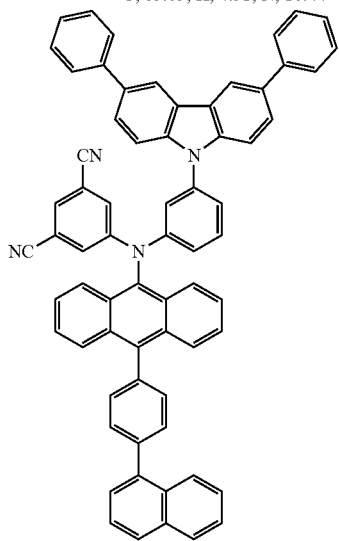

C_68H_42N_4
Exact Mass: 914.34
Mol. Wt.: 915.09
C, 89.25; H, 4.63; N, 6.12

Example 4

This example illustrates the preparation of Compound B4.

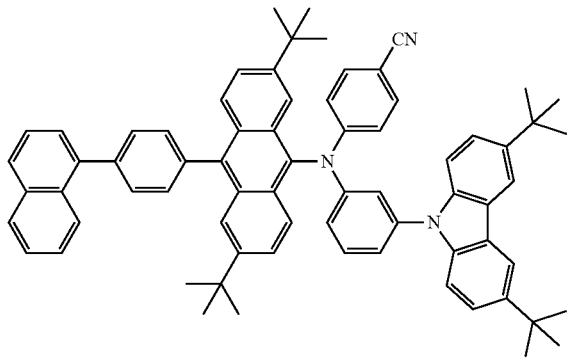

Chemical Formula: C_71H_67N_3
Exact Mass: 961.53
Molecular Weight: 962.31

This molecule was made using the same procedures as described above for Example 2, substituting 2,6-di-t-butyl-9-bromoanthracene for 9-bromoanthracene and 3,6-di-t-butyl-carbazole for 3,6-diphenylcarbazole. The structure was confirmed by 1-H nmr spectroscopy.

DEVICE EXAMPLES

These examples demonstrate the fabrication and performance of OLED devices.

(1) Materials

HIJ-1 is an electrically conductive polymer doped with a polymeric fluorinated sulfonic acid. Such materials have been described in, for example, published U.S. patent applications US 2004/0102577, US 2004/0127637, US 2005/0205860, and published POT application WO 2009/018009.

HT-1 is a triarylamine-containing copolymer. Such materials have been described in, for example, published POT application WO 2009/067419.

Host-1 is a deuterated aryl anthracene, as described in published POT application WO 2010-099534, compound H1.

Dopant-1 is a bis(diarylamino)chrysene compound, as described in published POT application WO 2010-135403, compound E17.

ET-1 is a phenanthroline derivative

The devices had the following structure on a glass substrate:
anode=Indium Tin Oxide (ITO), 50 nm
hole injection layer=HIJ-1 (50 nm)
hole transport layer=HT-1 (20 nm)
photoactive layer is discussed below (40 nm);
electron transport layer=ET-1 (10 nm)
electron injection layer/cathode=CsF/Al (0.7/100 nm)

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of a hole transport material, and then heated to remove solvent. After cooling the substrates were spin-coated with solution of the photoactive layer materials in methyl benzoate and heated to remove solvent. The substrates were masked and placed in a vacuum chamber. The electron transport layer was deposited by thermal evaporation, followed by a layer of CsF. Masks were then changed in vacuo and a layer of μl was deposited by thermal evaporation. The chamber was vented, and the devices were encapsulated using a glass lid, dessicant, and UV curable epoxy.

(3) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Example 1 and Comparative Example A

This example illustrates the use of a compound having Formula I as a hole trapper.

In Example 1, the photoactive layer was Host-1:Dopant-1 in a 13:1 weight ratio, with 1% by weight of Compound B2 as and electron trapper.

In Comparative Example A, the photoactive layer was Host-1:Dopant-1 in a 13:1 weight ratio, with no electron trapper.

The results are given in Table 1 below.

TABLE 1

Device results

| Ex. | CIE (x, y) | Voltage (V) | C.E. (cd/A) | E.Q.E. (%) | Projected Lifetime T50 @1000 nits |
|---|---|---|---|---|---|
| Comp. A | 0.136, 0.134 | 3.6 | 6.6 | 6.1 | 10907 |
| Ex. 1 | 0.136, 0.134 | 3.7 | 6.4 | 5.9 | 26309 |

All data @ 1000 nits,
CE = current efficiency;
CIEx and CIEy are the x and y color coordinates according to the C.I.E. chromaticity scale (Commission Internationale de L'Eclairage, 1931).
Projected T50 is the time in hours for a device to reach one-half the initial luminance at 1000 nits, calculated using an acceleration factor of 1.8.

It can be seen from Table 1 that the lifetime is greatly increased when the compound having Formula I is present as a hole trapper.

Example 2 and Comparative Example B

This example illustrates the use of a compound having Formula as an emissive material.

In Example 1, the photoactive layer was Host-1:Compound B2 in a 13:1 weight ratio.

In Comparative Example B, the photoactive layer was Host-1:Dopant-1 in a 13:1 weight ratio.

The results are given in Table 2 below.

TABLE 2

Device results

| Ex. | CIE (x, y) | Voltage (V) | C.E. (cd/A) | E.Q.E. (%) | Projected Lifetime T50 @1000 nits |
|---|---|---|---|---|---|
| Comp. B | 0.135, 0.142 | 3.6 | 7.1 | 6.3 | 12211 |
| Ex. 2 | 0.138, 0.143 | 4.2 | 4.8 | 4.2 | 27138 |

All data @ 1000 nits,
CE = current efficiency;
CIEx and CIEy are the x and y color coordinates according to the C.I.E. chromaticity scale (Commission Internationale de L'Eclairage, 1931).
Projected T50 is the time in hours for a device to reach one-half the initial luminance at 1000 nits, calculated using an acceleration factor of 1.8.

It can be seen from Table 2 that the lifetime is greatly increased when the compound having Formula I is present as the emissive material.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An electroactive compound having Formula II

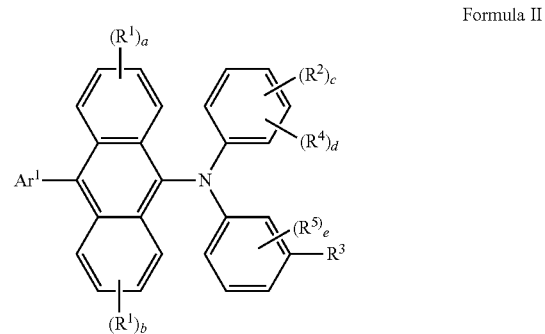

Formula II wherein:
Ar$^1$ is an aryl group;
R$^1$ is the same or different at each occurrence and is D, alkyl or aryl;
R$^2$ is an electron-withdrawing group;
R$^3$ is H, D, carbazolyl, diarylamino, an electron-withdrawing group, or a deuterated analog thereof;
R$^4$ is the same or different at each occurrence and is cyano, nitro, or —SO$_2$R, where R is alkyl, or a deuterated analog thereof;
R$^5$ is the same or different at each occurrence and is D, alkyl, alkoxy, silyl, siloxane, an electron-withdrawing group, or a deuterated analog thereof;
a is an integer from 0 to 4;
b is an integer from 0 to 4;
c is an integer from 1 to 5;
d is an integer greater than 0, such that c+d≤5; and
e is an integer from 0 to 4
and further wherein the compound has a LUMO level deeper than −2.3 eV and a band gap of at least 2.9 eV.

2. The compound of claim 1, wherein Ar$^1$ is phenyl, biphenyl, naphthyl, binaphthyl, phenylnaphthyl, naphthylphenyl, a substituted derivative thereof, or a deuterated analog thereof.

3. The compound of claim 1, wherein R$^1$=D and a and b are both greater than 0.

4. The compound of claim 1, wherein R$^2$ is cyano, nitro, or —SO$_2$R, where R is alkyl.

5. The compound of claim 1, wherein $R^3$ is carbazolyl, diphenylamino, or a deuterated analog thereof.
6. The compound of claim 1, wherein e=0.
7. The compound of claim 1, wherein d=1 and $R^2=R^4=CN$.
8. A compound selected from compound B1 through B11
Compound B1
Compound B2
Compound B3
Compound B4
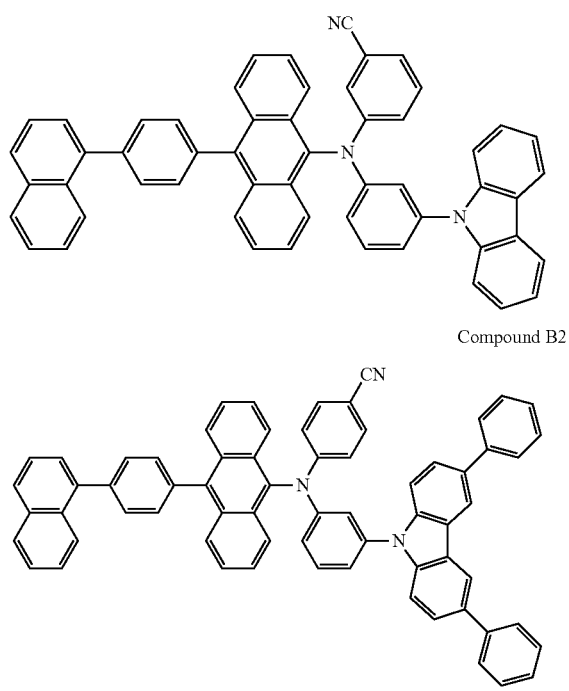
Compound B5
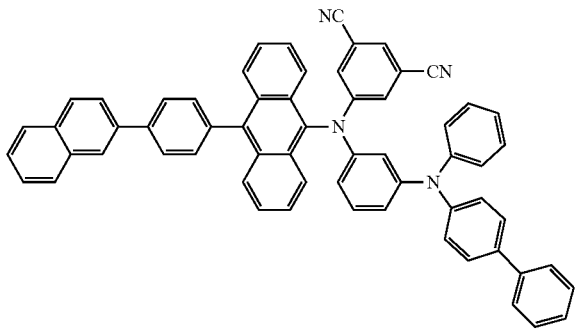
Compound B6
Compound B7
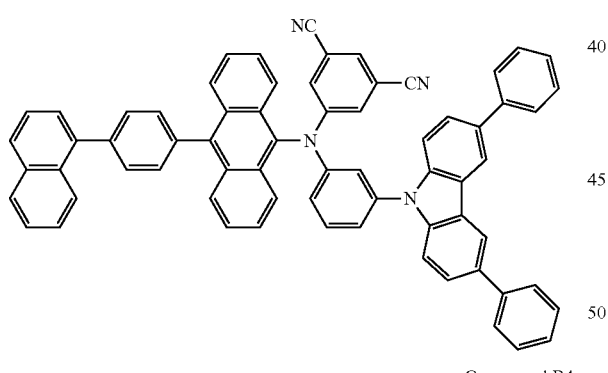
Compound B8
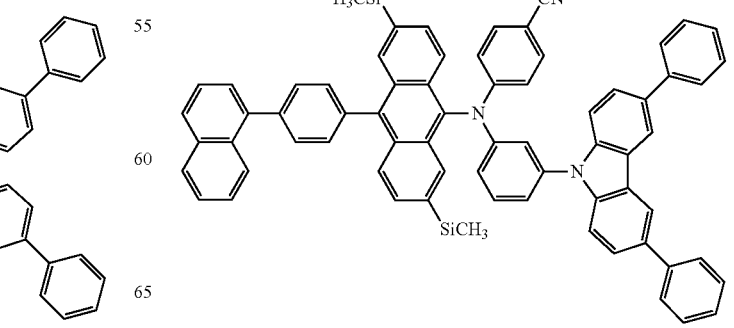
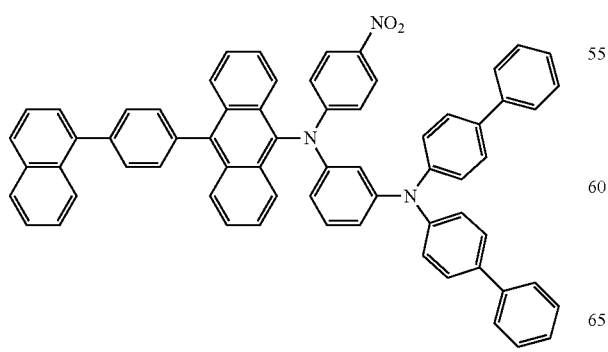

-continued

Compound B9

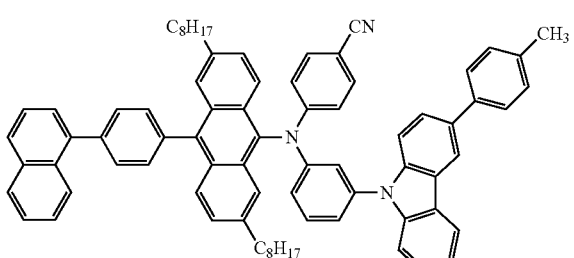

Compound B10

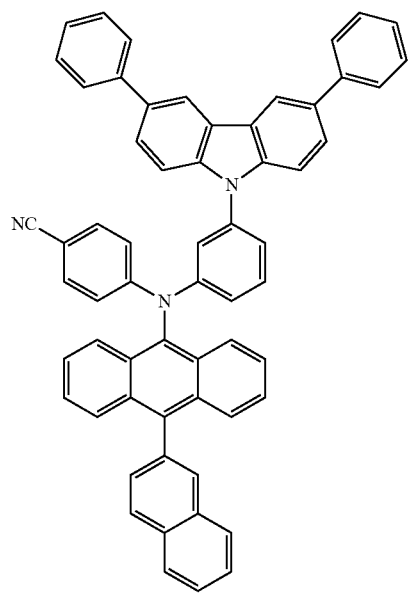

Compound B11

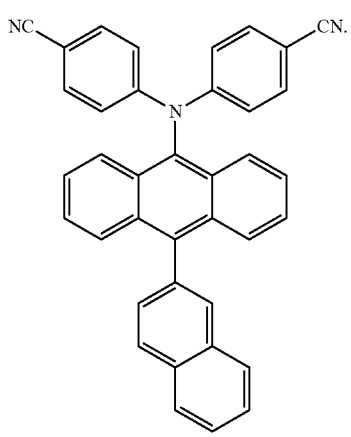

9. An organic electronic device comprising a first electrical contact, a second electrical contact and a photoactive layer therebetween, the photoactive layer comprising an electroactive compound having Formula II

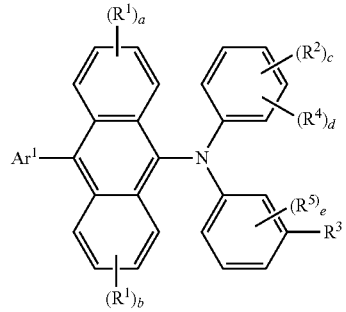

Formula II wherein:
- $Ar^1$ is an aryl group;
- $R^1$ is the same or different at each occurrence and is D, alkyl or aryl;
- $R^2$ is an electron-withdrawing group;
- $R^3$ is H, D, carbazolyl, diarylamino, an electron-withdrawing group, or a deuterated analog thereof;
- $R^4$ is the same or different at each occurrence and is cyano, nitro, or —$SO_2R$, where R is alkyl, or a deuterated analog thereof;
- $R^5$ is the same or different at each occurrence and is D, alkyl, alkoxy, silyl, siloxane, an electron-withdrawing group, or a deuterated analog thereof;
- a is an integer from 0 to 4;
- b is an integer from 0 to 4;
- c is an integer from 1 to 5;
- d is an integer greater than 0, such that c+d≤5; and
- e is an integer from 0 to 4 and further wherein the compound has a LUMO level deeper than −2.3 eV and a band gap of at least 2.9 eV.

10. The device of claim 9, wherein the photoactive layer comprises the electroactive compound of Formula II and further comprises a host material.

11. The device of claim 9, wherein the photoactive layer consists essentially of the electroactive compound of Formula II and a host material.

12. The device of claim 9, wherein the photoactive layer comprises a blue luminescent compound, a host material, and a compound having Formula II.

13. The device of claim 9, wherein the photoactive layer consists essentially of a blue luminescent compound, a host material, and a compound having Formula II.

* * * * *